United States Patent [19]

Seedhom et al.

[11] Patent Number: 4,775,380
[45] Date of Patent: Oct. 4, 1988

[54] SURGICAL REPLACEMENT OF LIGAMENTS

[76] Inventors: Bahaa B. Seedhom, 75 Holt Park Crescent, Leeds, West Yorkshire, LS16 7SL, England; Kyosuke Fujikawa, Department of Orthopaedic Surgery, Keio School of Medicine, Tokyo, Japan

[21] Appl. No.: 919,669

[22] Filed: Oct. 16, 1986

[30] Foreign Application Priority Data

Oct. 17, 1985 [GB] United Kingdom ............... 8525565

[51] Int. Cl.⁴ .............................................. A61F 1/00
[52] U.S. Cl. ........................................ 623/12; 623/13; 623/18; 128/334 R
[58] Field of Search ................ 623/12, 13, 16, 18, 623/20; 128/334 R, 335.5

[56] References Cited

U.S. PATENT DOCUMENTS

| | | | |
|---|---|---|---|
| 3,545,008 | 12/1970 | Bader, Jr. | 623/13 |
| 3,842,441 | 10/1974 | Kaiser | 623/13 |
| 4,455,690 | 6/1984 | Homsy | 623/13 X |
| 4,605,414 | 8/1986 | Czajka | 623/13 |

FOREIGN PATENT DOCUMENTS

| | | | |
|---|---|---|---|
| 126520 | 11/1984 | European Pat. Off. | 623/13 |
| 0153831 | 2/1985 | European Pat. Off. | 623/13 |
| 2747568 | 4/1979 | Fed. Rep. of Germany | 623/13 |
| 1178441 | 9/1985 | U.S.S.R. | 623/13 |
| 8404669 | 12/1984 | World Int. Prop. O. | 623/13 |

OTHER PUBLICATIONS

Artificial Tendons Early Development and Application, article by James Hunter, American Journal of Surgery, vol. 109, pp. 325-338, (3-1965).

*Primary Examiner*—Richard J. Apley
*Assistant Examiner*—David J. Bender
*Attorney, Agent, or Firm*—Mason, Kolehmainen, Rathburn & Wyss

[57] ABSTRACT

A prosthetic ligament for implantation between at least two bones and which takes the form of a tubular body made of woven flexible material through which tissue ingrowth can take place after implantation. A cord is attached to one end of the ligament to thread and to pull the ligament through channels formed in the bones, and a protective detachable sheath is attached to the ligament in order to facilitate the implantation of the ligament as it is pulled through the channels, the sheath immediately thereafter being detached. A bone plug introducer is used to insert a bone plug into one end of the ligament within the bone tunnel, which thereby secures the ligament end in position.

9 Claims, 8 Drawing Sheets

SURGICAL REPLACEMENT OF LIGAMENTS

FIELD OF THE INVENTION

The present invention relates to improvements in an implantable device, a method and surgical instrument for the surgical replacement of a ligament, and in particular in a method for inserting a prosthetic ligament into the body.

DESCRIPTION OF PRIOR ART

European Patent Application No. 85300931.4 (publication No. 0153831A) of the applicants describes a surgical method with reference to the replacement of an anterior cruciate ligament in the knee. The method involves the use of an artificial ligament of woven polyester yarn in the form of a tube having a longitudinal slit at each end of the ligament. One of the slits extends to one end of the ligament, and at the other end of the ligament, at the end of that slit which is remote from the centre of the ligament, is a closure which seals off the tube, thus providing a pouch structure for accommodating a bone plug.

The method also involves the use of a set of surgical tools to enable the ligament to be inserted into the knee. These comprise a clamp for guiding a cylindrical reaming tool along a predetermined axis to form a replaceable bone plug from a host bone, a cylindrical reaming tool adapted to sever the base of the plug from the host bone, a push rod to aid removal of the plug from the reaming tool and to aid reinsertion of the bone plug into the host bone and a cylindrical drill bit guide for allowing a reduced diameter bore to be drilled from the base of the socket from which the bone plug has been removed, to the other side of the bone.

The method comprises locating the guide clamp on one side of a first bone, for example a femur, removing a cylindrical bone plug from the femur, and drilling a reduced diameter bore from the base of the socket to the other side of the femur. The same process is then repeated on the tibia.

The ligament, which has a threading cord attached to the pouch end, is then threaded through the channels formed by the sockets and bores in the tibia and femur until the pouch is exposed. The bone plug previously removed from the femur is then placed in the pouch. Once the plug is located within the pouch, the ligament is pulled back in the opposite direction, and this results in the bone plug being forced against the shoulder between the socket and the bore in the femur. The bone plug from the tibia is then pushed into the other slit at the other end of the ligament with the aid of the push rod, so that the ligament is secured by bone plugs within both the femur and the tibia.

One of the problems with this method is that distortions of the relatively loose structure of the ligament can occur as it is drawn through the channels in the tibia and the femur due to snagging of the woven material on the rough inner surface of the bone channels. In addition, the ligament may tend to drag bone fragments along the tunnels and into the intra-articular section, which is a disadvantage in this section where soft tissue only is required. The distortion of the ligament as it is drawn through the tunnels, is also inconvenient to the surgeon.

Also, it is sometimes difficult to replace the tibial bone plug since it can snag against the loose structure of the ligament. Since the plug is introduced into the tibial tunnel in a direction opposite to that of the tension along the ligament, the latter might be slack within the joint at the end of the surgical procedure. The absence of adequate tension along the ligament within the joint makes it redundant.

It is therefore the purpose of the present invention to provide an improved ligament and a tool which attempts to overcome these disadvantages.

SUMMARY OF THE INVENTION

According to a first aspect of the present invention there is provided a prosthetic ligament which comprises a flexible elongate body adapted for implantation between at least two bones, pulling means attached to one end of the body for threading and for pulling the ligament through channels formed in the bones, and a detachable sheath of flexible material extending substantially along the whole of the length of the body of the ligament, said sheath being attached initially to the ligament for joint movement with the ligament through the channels in the bones and thereafter being detachable from the ligament to allow the sheath to be removed.

Thus, the sheathed ligament can be pulled easily through the channels in two bones, such as a tibia and femur without snagging, and the ligament is protected from damage and deformation.

Conveniently the pulling means comprises a cord which is attached to one end of the ligament.

Preferably the sheath extends a little way beyond the point of attachment of the cord to the ligament body and the cord is knotted in a first knot within the sheath.

In addition, the cord may be knotted around the sheath at a second knot, further away from the point of attachment of the cord than the first knot, the function of the second knot being to hold the sheath secure and prevent it slipping around the ligament as it is pulled through the channels.

Other means may be adopted to secure the cord to the sheath such as, for example, application of a metal crimp around the cord and the sheath.

The sheath may extend a little way beyond the other end of the ligament to provide a grip portion.

The sheath may be in the form of a tube (preferably made of polyethylene), but alternatively it may be more than one separate piece of material, for example strips of material covering each side of the ligament.

According to a further aspect of the present invention there is further provided a method of implanting a prosthetic ligament between at least two bones, the ligament having a flexible elongate body and means attached to one end of the body of the ligament whereby it may be threaded and subsequently pulled through channels in the bones, the method comprising surrounding the ligament prior to implantation with a sheath of flexible material extending substantially along the whole of the length of the body of the ligament, securing the sheath to the ligament at one end thereof, to prevent relative movement between the sheath and the ligament, forming channels in each of the bones as described above, threading and subsequently pulling the sheathed ligament through the channels, cutting the sheath at a position adjacent the point of attachment of the threading means to the ligament body so that the sheath is free to slide relative to the ligament, relatively withdrawing the sheath from the ligament, and then replacing the bone plugs as described above.

DESCRIPTION OF PREFERRED EMBODIMENTS

Figure 1:
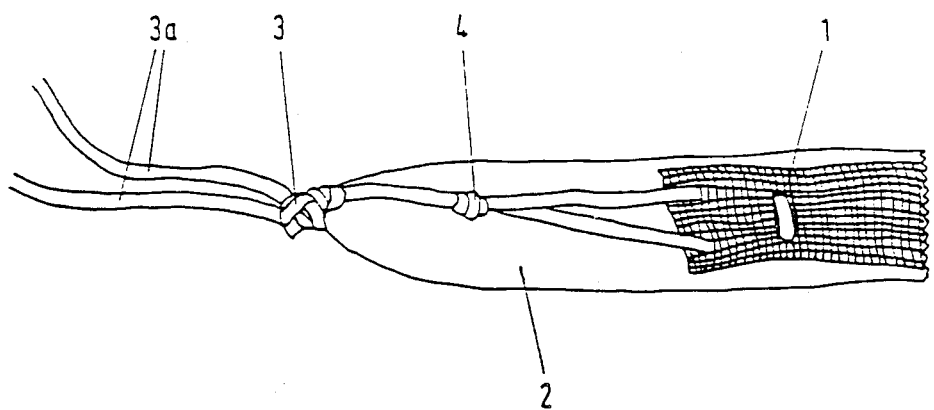
FIG. 1 shows the closed end of one embodiment of ligament with a sheath secured thereto.

Referring to FIG. 1, a ligament 1 of the present invention takes the form of an elongate strip of open weave polyester yarn which is formed into a tube. One example of a possible construction of the ligament 1 is shown in more detail in published European specification No. 0153831A which takes the form of a perforated tube open at one end, and having a pouch at its opposite end.

The ligament 1 is provided with sheath 2 in the form of a tube made from polyethylene sheet. The sheath 2 completely surrounds the ligament 1 along all of its length, and is secured at the closed end of the ligament by means of a knot 3 in the cord 3a which is attached to the closed end of the ligament. The knot 3 is knotted around the outside of the sheath 2 to secure it in place and prevent sliding of the sheath 2 with respect to the ligament 1. The cord 3a is also knotted within the sheath in a knot 4.

Figure 2:
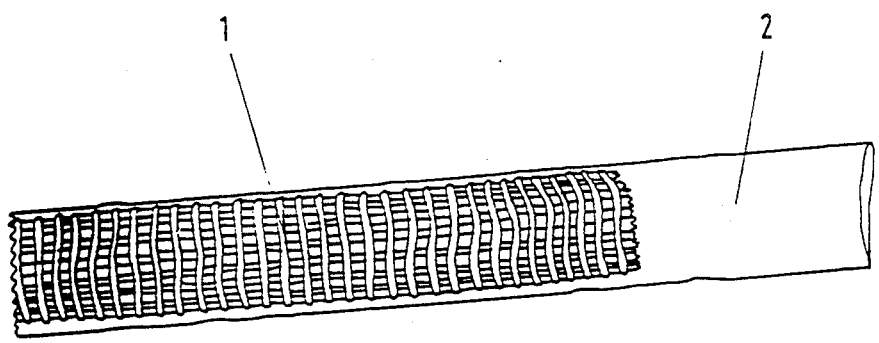
FIG. 2 shows the open end of the ligament surrounded by the sheath.

Referring to FIG. 2, the opposite end of the sheath is open and extends a little way beyond the open end of the ligament.

Figure 3:
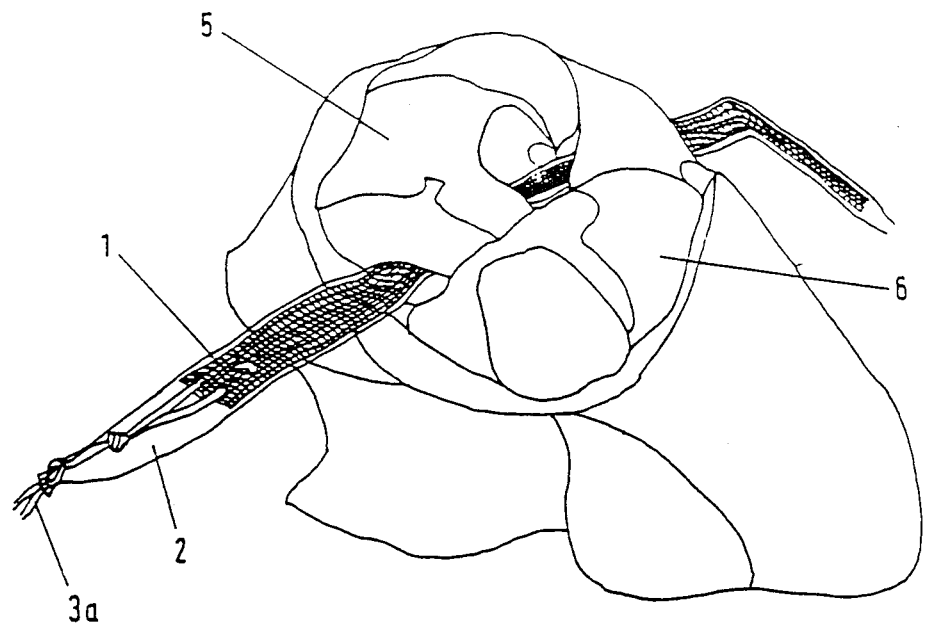
FIG. 3 shows the sheathed ligament being threaded through the channels in the tibia and femur.

Referring to FIG. 3, after the surgical operation of removing bone plugs from the femur 5 and the tibia 6 and drilling holes extending from the base of each of the sockets to the opposite side of the respective bone, the sheathed ligament is threaded through the channels, first through the tibia and then through the femur by means of pulling on the cord 3a. The sheath 2 serves to protect the ligament 1 as it is pulled through the channels in the bones, and also allows easy passage of the ligament through the bones without snagging of the ligament material.

Figure 4:
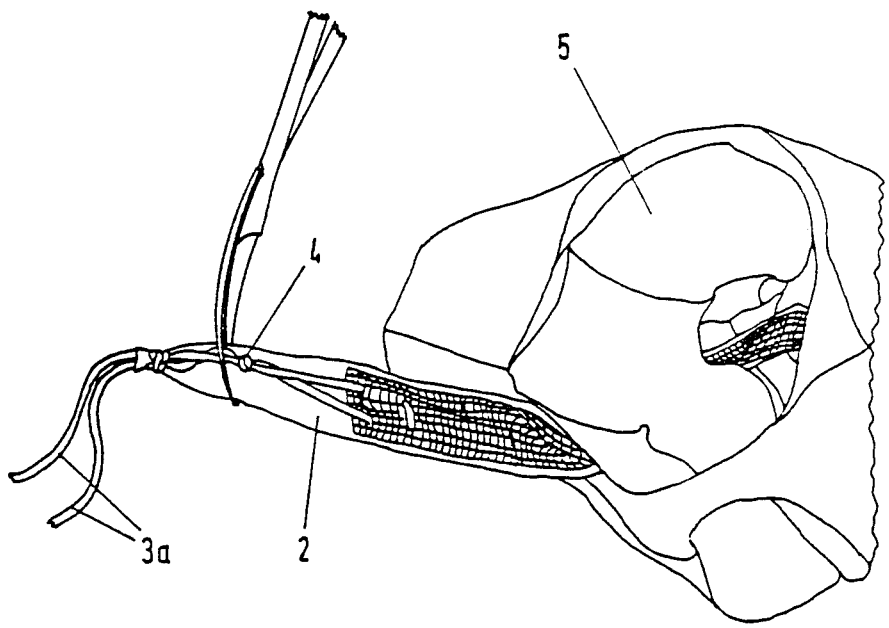
FIG. 4 shows the sheath and cord being cut.

Referring now to FIG. 4, once the ligament has been threaded through the bones, the sheath 2 and the cord 3a are cut just above the knot 4. This allows the sheath to side freely with respect to the ligament.

Figure 5:
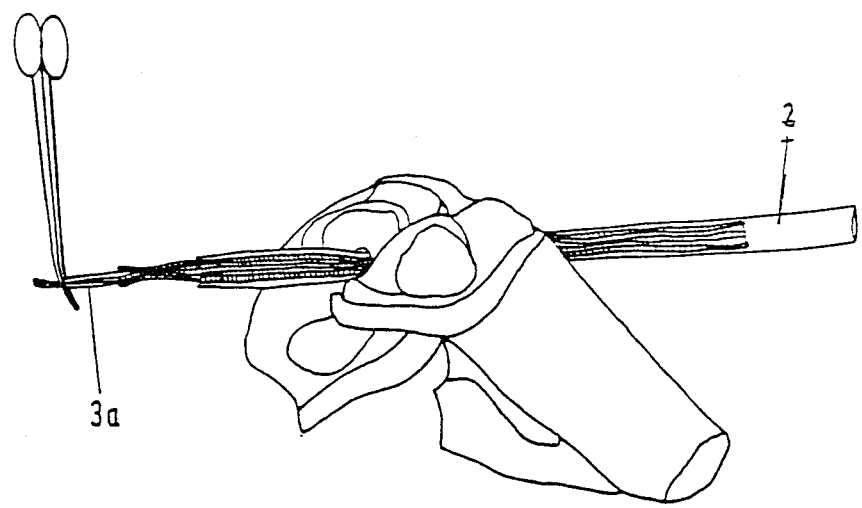
FIG. 5 shows the ligament being pulled taut and the sheath being withdrawn from the ligament.

Referring now to FIG. 5, the ligament is pulled taut by holding the cord 3a and at the same time pulling on the sheath 2 at the open end of the ligament.

Figure 6:
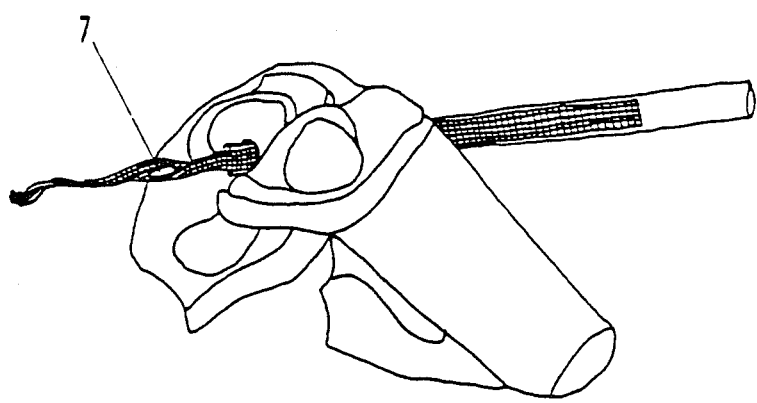
FIG. 6 shows the bone plug being placed within the pouch of the ligament.

Referring to FIG. 6, the sheath is partly withdrawn from the ligament, exposing the pouch, and the femoral bone plug is placed into the pouch 7 at the closed end of the ligament.

Figure 7:
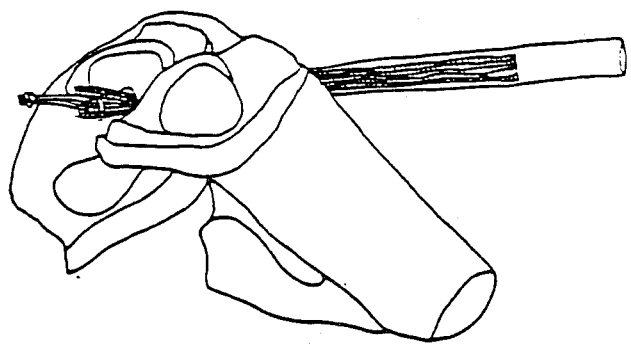
FIG. 7 shows the ligament being pulled to secure the femoral bone plug in place in the femur.

Referring to FIG. 7, the ligament is then pulled at the open end causing the bone plug in the pouch to be pulled into place within the pouch in the femoral socket.

Figure 8:
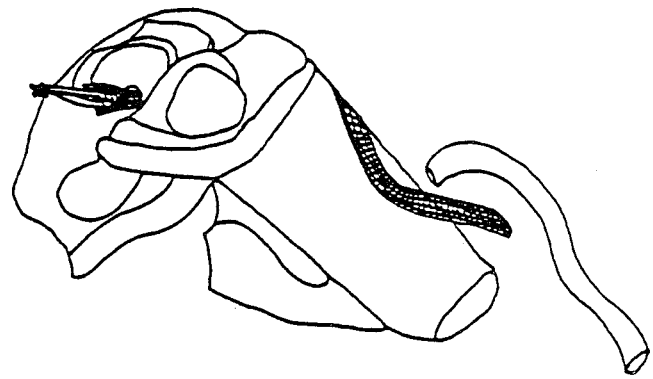
FIG. 8 shows the implanted ligament with the sheath completely withdrawn.

FIG. 8 shows the ligament having had the sheath completely withdrawn from it and the femoral bone plug in place.

Figure 9:
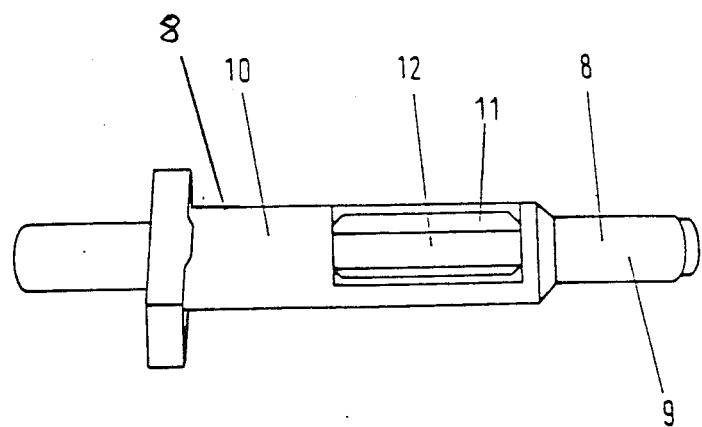
FIG. 9 shows the bone plug introducer with the plunger in its extended position.
Figure 10:
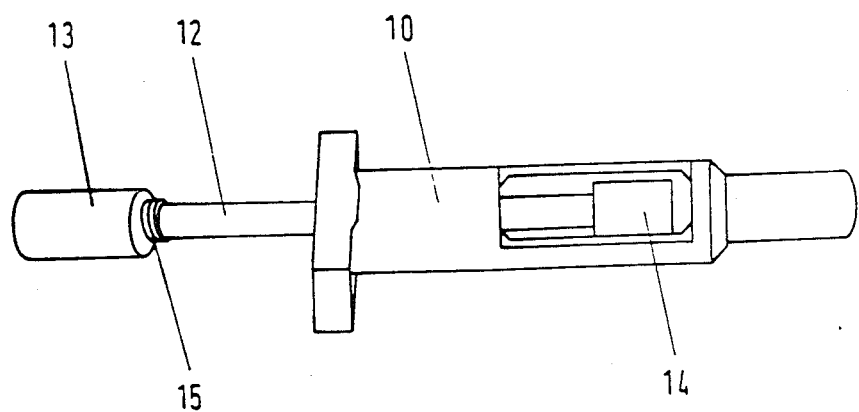
FIG. 10 shows the bone plug introducer with its plunger in a partially retracted position.

Referring to FIGS. 9 and 10, a bone plug introducer of the present invention comprises a hollow cylindrical body 8 within which is located a plunger 12. The body 8 comprises a thin walled section 9 having an open end, and a thicker walled section at the opposite end, a space 11 being defined between these two sections 9 and 10 to allow a bone plug to be inserted within the hollow body. The plunger 12 has two end portions 13 and 14, and at the end 13 there may be provided a threaded portion 15 for engagement within a corresponding threaded portion in the thick wall section 10 of the cylindrical body. The bone plug introducer may be made from metal, or alternatively from disposable plastics material.

Figure 11:
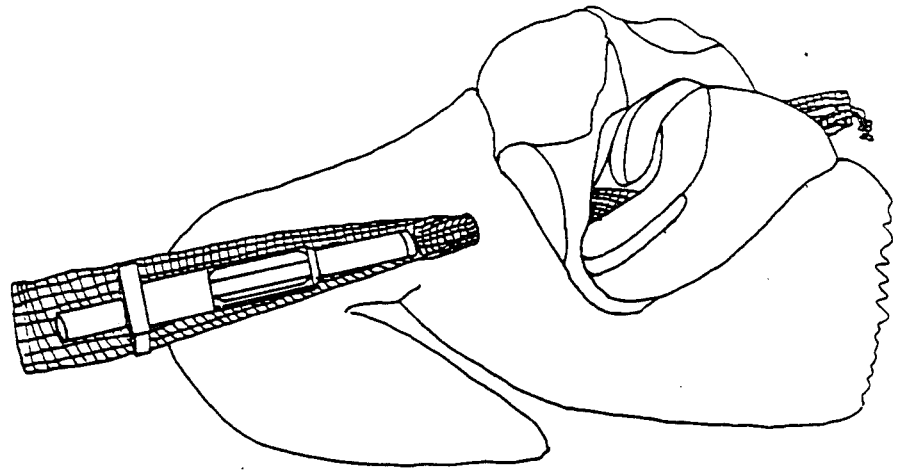
FIG. 11 shows the bone plug introducer being inserted into the open end of the ligament.

Referring to FIG. 11, the bone plug introducer is placed in position within the open end of the ligament, the plunger being in its extended position.

Figure 12:
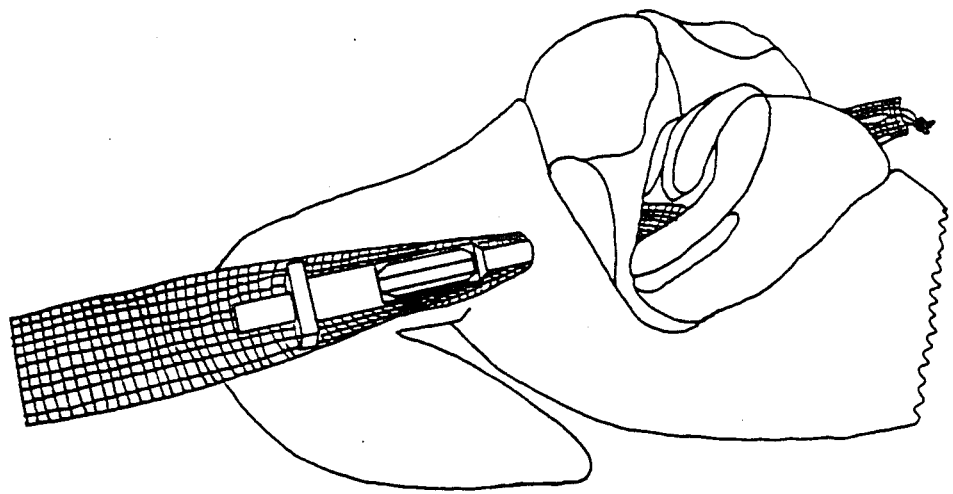
FIG. 12 shows the bone plug introducer being pushed to the bottom of the socket in the bone.

Referring to FIG. 12 the thin wall section 9 is pressed against the socket in the tibia whilst keeping the ligament under tension.

Figure 13:
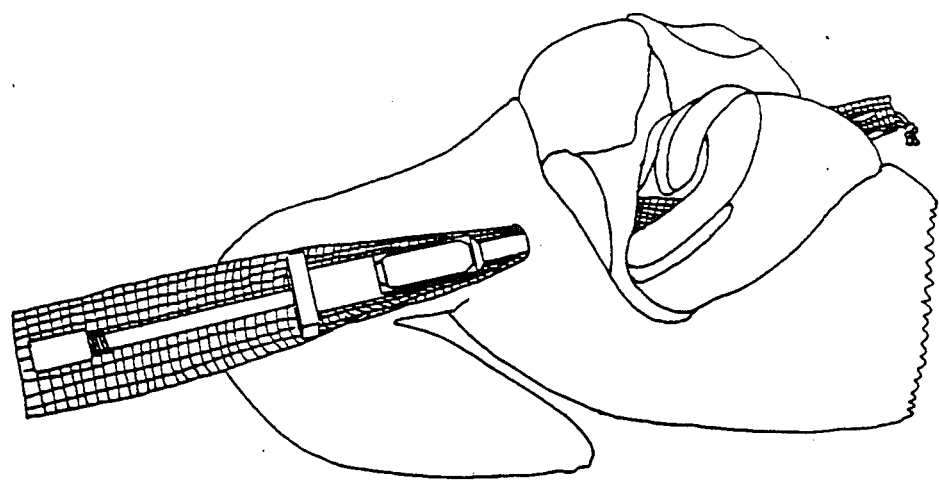
FIG. 13 shows the plunger withdrawn to accommodate the bone plug.
Figure 14:
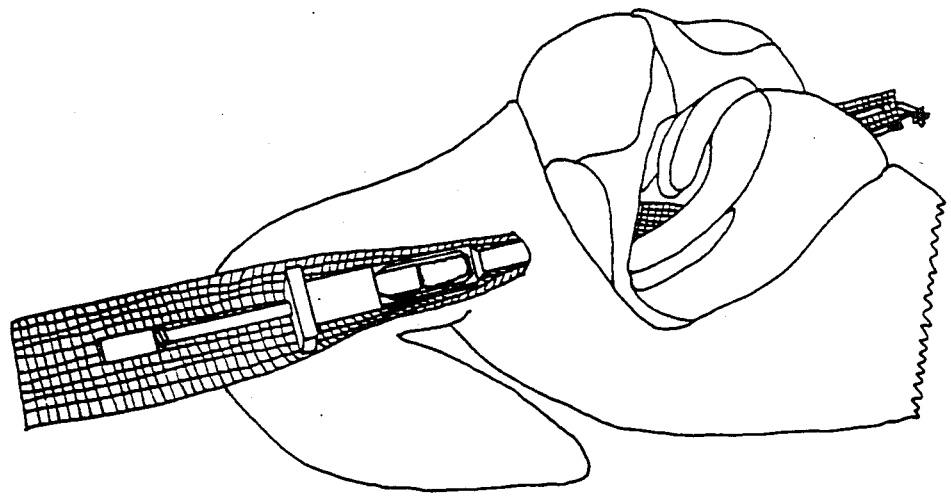
FIG. 14 shows the bone plug introducer with the bone plug inside it.

Referring to FIG. 13, the plunger is then retracted to define a space within which the tibial bone plug is then placed. Referring to FIG. 14, the plunger is then pushed in towards the tibial socket, and the bone plug is ejected from the body into the socket.

Figure 15:
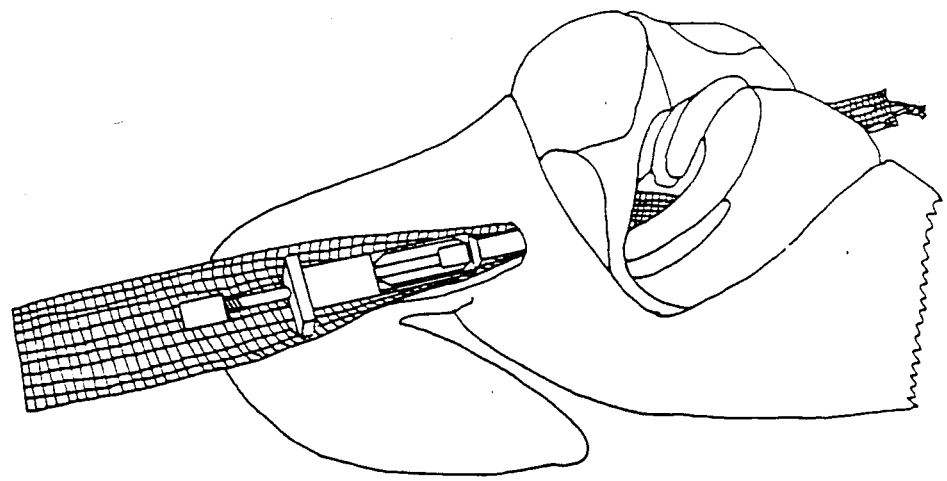
FIG. 15 shows the plunger being pushed to insert the bone plug within the socket in the host bone; and, FIG. 16 shows the bone plug introducer being withdrawn leaving the plug in the correct position.
Figure 16:
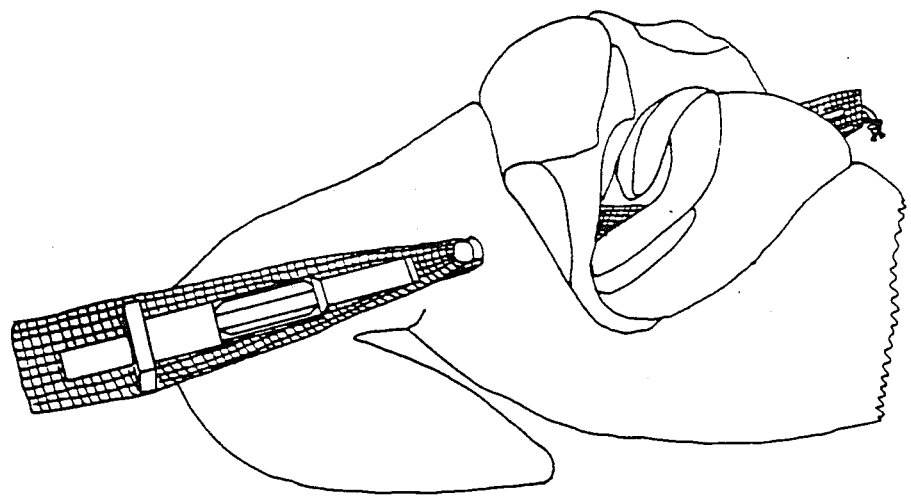

Referring to FIGS. 15 and 16, once the bone plug is in place in the tibia, the ligament is retained in the tension whilst the bone plug introducer is withdrawn, keeping the plunger pushed in. Thus, with a bone plug introducer of the present invention, the tibial bone plug may be replaced in the tibial socket without causing distortion in the ligament, by snagging against it, whilst retaining adequate tension in the ligament.

We claim:

1. A prosthetic ligament which comprises a flexible elongate body adapted for implantation between at least two bones, a cord attached to one end of the body for threading through channels formed in the bones, and a detachable sheath of flexible material extending substantially along the whole of the length of the body of the ligament, said sheath extending beyond the attachment of the cord to the ligament body and being attached initially to the ligament for joint movement through the channels in the bones and thereafter being detachable from the ligament to allow the sheath to be removed immediately after implantation of the ligament, and the cord being knotted in a first knot within the sheath.

2. A prosthetic ligament according to claim 1, in which the cord is connected to the sheath by means of a second knot, said second knot being located further away from the point of attachment of the cord to the ligament body than the first knot.

3. A prosthetic ligament according to claim 1, in which the sheath is in the form of a tube.

4. A prosthetic ligament according to claim 1, in which the sheath is made from polyethylene.

5. A prosthetic ligament which comprises a flexible elongate body adapted for implantation between at least two bones, elongate pulling means attached to one end of the body for threading through channels formed in the bones, and a detachable sheath of flexible material extending substantially along the whole of the length of the body of the ligament, said sheath extending in one direction beyond the attachment of the elongate pulling means to the ligament body and in an opposite direction beyond the opposite end of the ligament body to provide a gripping portion, and said sheath being attached initially to the ligament for joint movement through the channels in the bones and thereafter being detachable from the ligament by pulling said gripping portion to allow the sheath to be removed immediately after implantation of the ligament.

6. A prosthetic ligament according to claim 5, in which the elongate pulling means comprises a cord.

7. A method of implanting a prosthetic ligament between at least two bones wherein the ligament comprises a flexible elongated body, elongate pulling means attached to one end of the body for threading through channels formed in the bones, and a detachable sheath of flexible material extending substantially along the whole of the length of the body of the ligament and in one direction beyond the attachment of the elongate pulling means to the body and in an opposite direction beyond the opposite end of the body to provide a gripping portion, said method comprising the steps of surrounding the ligament with said sheath prior to implantation, securing the sheath to the ligament at one end thereof to prevent relative movement between the sheath and the ligament, extracting plugs of bone and forming channels in each of the bones, threading and subsequently pulling the sheathed ligament through the channels in the bones by means of said elongate pulling means, cutting the sheath at a position adjacent to the point of attachment of the elongate pulling means to the ligament body so that the sheath is free to slide relative to the ligament, withdrawing the sheath from the ligament by pulling said gripping portion and then introducing the bone plugs into the bone channels.

8. A method according to claim 7, in which one of the bone plugs is inserted into a pouch formed in the ligament, and is introduced into the mouth of a respective bone channel as the ligament is pulled through the channels.

9. A method according to claim 8, in which the other bone plug is introduced into the mouth of the other bone channel by means of a bone plug introducer.

* * * * *